United States Patent [19]

Klingler et al.

[11] 4,196,298

[45] Apr. 1, 1980

[54] CYCLIC SULFONIUM YLIDS

[75] Inventors: Thomas C. Klingler, Baton Rouge, La.; Donald L. Schmidt, Midland, Mich.

[73] Assignee: The Dow Chemical Company, Midland, Mich.

[21] Appl. No.: 958,275

[22] Filed: Nov. 6, 1978

Related U.S. Application Data

[63] Continuation-in-part of Ser. No. 592,841, Jul. 2, 1975, abandoned.

[51] Int. Cl.² .................... C07D 333/24; C08L 51/00
[52] U.S. Cl. .......................................... 549/77; 549/60
[58] Field of Search .................. 260/332.3 R, 332.2 A

[56] References Cited

U.S. PATENT DOCUMENTS 3,915,991  10/1975  Schmidt et al. .................. 260/332.3

*Primary Examiner*—Alan Siegel

*Attorney, Agent, or Firm*—L. Wayne White; James B. Guffey

[57] ABSTRACT

Novel cyclic sulfonium ylids corresponding to the formula

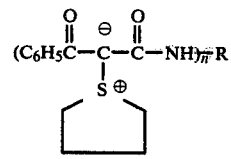

I wherein R is a hydrocarbylene radical (or a hydrocarbylene radical whose chain length is interrupted by an atom of oxygen or sulfur) of from 2 to about 20 carbon atoms, are useful as cross-linking agents for carboxyl-containing polymers. The compounds are conveniently prepared by reacting phenacyltetrahydrothiophenium bromide with the corresponding hydrocarbylene diisocyanate in the presence of a strong base (e.g. sodium hydride) and anhydrous tetrahydrofuran.

8 Claims, No Drawings

CYCLIC SULFONIUM YLIDS

CROSS-REFERENCE TO RELATED APPLICATION

This application is a continuation-in-part of our copending application Ser. No. 592,841, filed July 2, 1975 (now abandoned).

BACKGROUND OF THE INVENTION

The reaction of carboxy-containing polymers with various cyclic sulfonium compounds has been previously described. See, for example, the commonly owned U.S. Pat. applications Ser. Nos. 382,976 and 382,977 (both filed on July 26, 1973) and Ser. No. 393,855 (filed Sept. 4, 1973) by Schmidt, Smith, Hatch, and Broxterman. The cyclic sulfonium salts there used, however, are structurally dissimilar to the novel class of compounds here defined.

SUMMARY OF THE INVENTION

We have discovered a novel class of cyclic sulfonium ylids which correspond to the formula

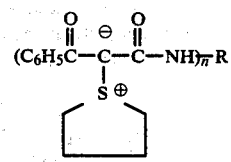
     I wherein R is a hydrocarbylene radical, or a hydrocarbylene radical whose chain length is interrupted by an atom of oxygen or sulfur, of from 2 to about 20 carbon atoms. The novel compounds are useful as cross-linking agents for carboxyl-containing polymers.

As used herein, the term "hydrocarbylene" is used in its conventional sense to designate a divalent hydrocarbon radical having each of its free valencies located on different carbon atoms. Thus, in the formula I above R can be a divalent hydrocarbon radical of from 2 to about 20 carbon atoms or, alternatively, R can be a divalent hydrocarbon radical of from 2 to about 20 carbon atoms whose chain length (which chain length, for example, can be made up of repeating units of one or more carbon atoms and which repeating units can be aliphatic, alicyclic or aromatic in character) is interrupted by an atom of oxygen or sulfur and in each such instance the two valencies of such divalent radical are located on different carbon atoms of such radical.

In formula I above, R is preferably an alkylene of from 2 to 6 carbon atoms, 2,4-tolylene (i.e.

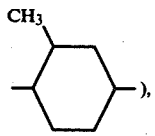

or 4,4'-oxydiphenylene (i.e. $-C_6H_4-O-C_6H_4-$).

The novel compounds are normally solids at ambient temperature and are slightly soluble in aromatic hydrocarbons (e.g. benzene, toluene, xylene, etc.) and soluble in methylene chloride, chloroform, tetrahydrofuran, and the like. They are quite reactive with carboxyl-containing compounds.

Compounds within I are conveniently prepared by reacting phenacyltetrahydrothiophenium chloride or bromide with the corresponding hydrocarbylene (or oxygen or sulfur interrupted hydrocarbylene) diisocyanate in the presence of a strong base (e.g. sodium hydride) and a suitable inert organic solvent (e.g. anhydrous tetrahydrofuran). This reaction is illustrated by the following equations:

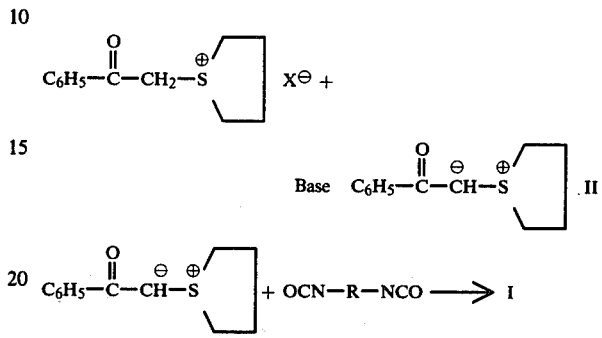

The reactants in the above process are well known compounds or classes of compounds having known methods of preparation. Phenacyltetrahydrothiophenium chloride or bromide, for example, is prepared by reacting $C_6H_5-C(O)-CH_2Cl$ (or Br) with tetrahydrothiophene. Methods of preparing the diisocyanate reactants are likewise well known (e.g. reaction of phosgene with $NH_2-R-NH_2$).

Any member of the known class of diisocyanates corresponding to the formula OCN—R—NCO, wherein R has the above meaning, can be used as a reactant in the above process. Examples of suitable such compounds include those wherein R is ethylene, 1,4-butylene, 1,6-hexylene, 2,4-phenylene, tolylene, ethyleneoxyethylene ($-CH_2CH_2OCH_2CH_2-$) ethylenethioethylene, propyleneoxypropylene, phenylenethiophenylene, phenylenemethylenephenylene (i.e., methylenediphenylene), and the like.

The following examples further illustrate the invention.

EXAMPLE 1

A slurry of phenacyltetrahydrothiophenium bromide (11.5 g; 4 mmol) in 200 ml of dry tetrahydrofuran was reacted with 57% sodium hydride (1.68 g; 40 mmol). Gas evolution ceased from the reaction mixture after one hour at ambient temperature. The reaction product II

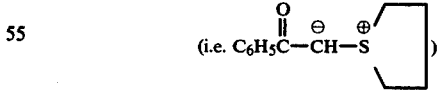

was thus obtained as a solution in tetrahydrofuran.

To the above solution was added oxydiphenylene isocyanate (i.e. $O+C_6H_4-NCO$); 5 g; 20 mmol) and the mixture stirred overnight at ambient conditions. Solid sodium bromide was filtered from the reaction mixture and the solvent removed under reduced pressure leaving the desired product as a yellow solid. The product was recrystallized twice in 100 ml portions of chloroform and precipitated with hexane giving 11.5 g (90 percent yield based on reactants charged) of the bisylid as a white powder and corresponding to the formula

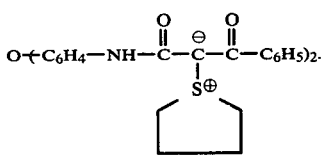

The product structure was confirmed by elemental analysis, infrared and nuclear magnetic resonance spectra.

EXAMPLE 2

A solution of II was prepared as in Example 1. Hexamethylene diisocyanate (2.52 g; 20 mmol) was added and the reaction mixture stirred at ambient temperature for approximately 72 hours. The solid NaBr was removed by filtration and washed with methylene chloride. The methylene chloride wash was combined with the tetrahydrofuran solution of the product and the organic solvents removed under reduced pressure. The resulting solid product was slurried in acetone, filtered and washed with acetone. The product was thus obtained as a white powder weighing 7.5 g (65% yield). An additional 2.2 g of product was later recovered from the acetone washes. The product was insoluble in water, slightly soluble in acetone and very soluble in methylene chloride and chloroform. The product structure corresponded to I wherein R is hexamethylene.

EXAMPLE 3

The procedure of Example 2 was essentially followed except here toluene diisocyanate (80% 2,4-isomer and 20% 2,6-isomer) was used as the isocyanate reactant. The crude product was recrystallized from a methylene chloride/acetone mixture and subsequently slurried in hot methanol, cooled, filtered and dried. The product was thus obtained as a white crystalline solid weighing 9.92 g (85% yield) melting at 227°–229° C. The product structure corresponded to I wherein R is tolylene. The product was insoluble in both acetone and water, slightly soluble in benzene and methanol, and very soluble in methylene chloride.

EXAMPLE 4

Phenacyltetrahydrothiophenium chloride (49 g; 0.1 mol) was added to solution of sodium hydroxide (16 g) in water (180 ml). The reaction mixture was stirred for 1.5 hours and extracted with 100 ml of chloroform. The chloroform layer (containing II) was isolated and blended with a solution of toluene diisocyanate (17.4 g; 0.2 mol) in 100 ml of chloroform. The reaction mixture was stirred for four hours at ambient temperature. Water (20 ml) was then added and the organic solvent removed under reduced pressure. The solid product thus obtained was slurried in hot methanol, cooled, filtered and dried. The product here obtained (50.93 g; 84% yield) had the same physical properties as the product of Example 3.

Utility as a Cross-linker

Compound III from Example 1 was dissolved in benzene and combined with a n-propanol solution of a vinyl addition interpolymer containing 12 mole percent acrylic acid, 55 mole percent butylacrylate and 33 mole percent methyl methacrylate which had been treated with ammonia to give a homogenous solution. This mixture was coated onto a metal panel and cured about 30 minutes at 80° C. and then 8 minutes at 130° C. The cured coating on the panel, thus produced, was insoluble in concentrated ammonium hydroxide.

Other compounds falling within formula I can be similarly prepared and used by reacting the ylid of II with other diisocyanates.

We claim:

1. A compound corresponding to the formula

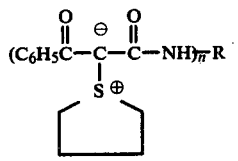

wherein R is a hydrocarbylene radical, or a hydrocarbylene radical whose chain length is interrupted by an atom of oxygen or sulfur, of from 2 to about 20 carbon atoms.

2. The compound defined by claim 1 in which R is ethylene, 1,4-butylene, 1,6-hexylene, 2,4-phenylene, tolylene, ethyleneoxyethylene, ethylenethioethylene, propyleneoxypropylene, phenylenethiophenylene or phenylenemethylenephenylene.

3. The compound defined by claim 1 in which R is phenylenemethylenephenylene.

4. A compound corresponding to the formula

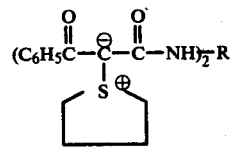

wherein R is alkylene of from 2 to 6 carbon atoms, 2,4-tolylene or oxydiphenylene.

5. The compound defined by claim 4 in which R is an alkylene of from 2 to 6 carbon atoms.

6. The compound defined by claim 4 in which R is 2,4-tolylene.

7. The compound defined by claim 4 in which R is oxydiphenylene.

8. A compound corresponding to the formula:

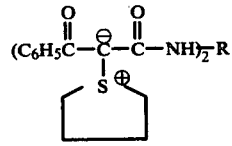

wherein R is a hydrocarbylene radical of from 2 to about 20 carbon atoms.

* * * * *

UNITED STATES PATENT AND TRADEMARK OFFICE
CERTIFICATE OF CORRECTION

PATENT NO. : 4,196,298
DATED      : April 1, 1980
INVENTOR(S): Thomas C. Klingler, et al.

It is certified that error appears in the above-identified patent and that said Letters Patent are hereby corrected as shown below:

At the title page under "Abstract"; at Col. 1, lines 25-30; and Col. 4, lines 20-25, the Formula is incorrect and should be shown as below:

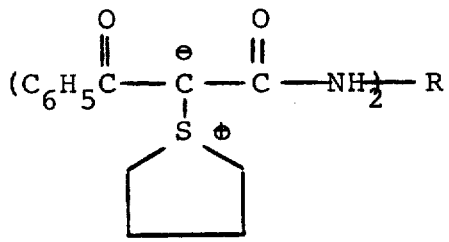

Signed and Sealed this

Fifteenth Day of July 1980

[SEAL]

Attest:

Attesting Officer

SIDNEY A. DIAMOND

Commissioner of Patents and Trademarks